United States Patent
Kraft et al.

(10) Patent No.: US 9,087,506 B1
(45) Date of Patent: Jul. 21, 2015

(54) PASSIVE ACOUSTICAL FILTERS INCORPORATING INSERTS THAT REDUCE THE SPEED OF SOUND

(71) Applicant: Doppler Labs, Inc., New York, NY (US)

(72) Inventors: Noah Kraft, Brooklyn, NY (US); Richard Fritz Lanman, New York, NY (US); Dan Wiggins, Montecito, CA (US); Jonathan Oswaks, Thousand Oaks, CA (US); Nils Jacob Palmborg, Brooklyn, NY (US)

(73) Assignee: Doppler Labs, Inc., New York, NY (US)

( * ) Notice: Subject to any disclaimer, the term of this patent is extended or adjusted under 35 U.S.C. 154(b) by 0 days.

(21) Appl. No.: 14/601,926

(22) Filed: Jan. 21, 2015

Related U.S. Application Data

(60) Provisional application No. 61/929,788, filed on Jan. 21, 2014.

(51) Int. Cl.
*H04R 1/40* (2006.01)
*G10K 11/16* (2006.01)
*G10L 21/0232* (2013.01)
*G10L 21/0208* (2013.01)
*H03G 3/32* (2006.01)
*H04R 1/22* (2006.01)
*H04R 1/10* (2006.01)
*H03G 9/02* (2006.01)
*H03G 5/16* (2006.01)

(52) U.S. Cl.
CPC .............. *G10K 11/16* (2013.01); *G10L 21/0208* (2013.01); *G10L 21/0232* (2013.01); *H03G 3/32* (2013.01); *H03G 5/165* (2013.01); *H03G 9/025* (2013.01); *H04R 1/1083* (2013.01); *H04R 1/22* (2013.01)

(58) Field of Classification Search
CPC ........ G10K 11/16; H04R 1/1083; H04R 1/22; H03G 3/32; H03G 9/025; H03G 5/165; G10L 21/0208; G10L 21/0232
USPC .................... 381/99, 94.1, 94.3, 72, 73.1, 321
See application file for complete search history.

(56) References Cited

U.S. PATENT DOCUMENTS

2006/0045284 A1* 3/2006 Haussmann et al. ............. 381/72

* cited by examiner

*Primary Examiner* — Paul S Kim
(74) *Attorney, Agent, or Firm* — SoCal IP Law Group LLP; John E. Gunther; Steven C. Sereboff

(57) ABSTRACT

There is disclosed a passive acoustical filter including a first filter element coupled between an ambient and an ear of a listener, at least a portion of the first filter element filled with a material in which a speed of sound is lower than a speed of sound in air.

14 Claims, 18 Drawing Sheets

PASSIVE ACOUSTICAL FILTERS INCORPORATING INSERTS THAT REDUCE THE SPEED OF SOUND

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

RELATED APPLICATION INFORMATION

This patent claims priority from the Provisional Patent Application No. 61/929,788, entitled PASSIVE AUDIO EAR FILTERS, filed Jan. 21, 2014.

BACKGROUND

1. Field

This disclosure relates generally to passive audio ear filters that can attenuate certain sound frequencies and allow other frequencies to pass through unchanged.

2. Description of the Related Art

Exposure to sound at certain sound pressure levels and sound frequencies can, over time, cause hearing loss.

Humans' perception to sound varies with both frequency and sound pressure level (SPL). For example, humans do not perceive low and high frequency sounds as well as they perceive midrange frequencies sounds (e.g., 500 Hz to 6,000 Hz). Further, human hearing is more responsive to sound at high frequencies compared to low frequencies. FIG. 1 illustrates equal loudness contours defined in ISO (International Standards Organization) Standard 226(2003). The X axis represents sound frequency measured in Hertz (Hz) and the Y axis represents sound pressure level measured in decibels (dB) relative to a pressure level of $2 \times 10^{-5}$ Pascal. The unit of measurement for loudness levels is the phon, and is arrived at by reference to equal-loudness contours. FIG. 1 shows equal loudness contours for loudness levels of 20, 40, 60, 80, and 100 phon. Each equal-loudness contour defines the sound pressure level, over the frequency spectrum, for which a listener perceives a constant loudness when presented with pure steady tones. FIG. 1 also shows the hearing threshold level.

Hearing protection that attenuates sound equally at all frequencies, or otherwise without regard to the variation of hearing sensitivity with frequency, may attenuate potentially damaging sounds at the expense of pleasurable sounds. For example, an ear filter providing uniform attenuation of 20 dB would reduce loudness by about 20 phon at 1 kHz and 40 phon at 20 Hz. Thus the relative loudness of low frequency sounds would be substantially reduced relative to the loudness of higher frequency sounds. However, with attention to the hearing response curves, it is possible to design ear filters that attenuate damaging sound levels and maintain, or even enhance, desired sounds.

There are many situations where people desire protection from sounds at certain frequencies, while allowing sounds at other frequencies to reach their ears. For example, at a concert, concert goers might want to enjoy the music, but also be protected from the mid-range and high levels of sound frequencies that cause damage to a person's hearing. On an airplane, passengers might wish to block out the roar of the engine, but not conversation. At a sports event, fans might desire to hear the action of the game, but receive protection from the roar of the crowd. While sleeping, people might want protection from all auditory disturbances. These are just a few common examples where people wish to hear some, but not all, of the sound frequencies in their environment.

DETAILED DESCRIPTION

Passive acoustical filters incorporating multiple filter elements can protect the ear from damaging sound frequencies while allowing less damaging sound frequencies to reach the ear. In this document, the term "filter element" refers to an acoustic filter that provides a single filter function such as a low-pass, high-pass, band-pass, or band-reject filter function. The term "passive acoustical filter" refers to a filter device that includes one or more filter element coupled between an ambient and a listener's ear. Two or more filter elements are considered to be "coupled between the ambient and the listener's ear" if ambient sound must pass through at least one of the filter elements before reaching the listener's ear. Two or more filter elements are considered to be "in series" if ambient sound must pass consecutively through all of the two or more filter elements before reaching the listener's ear. Two or more filter elements are considered to be "in parallel" if the filter elements provide alternate paths for ambient sound to reach the listener's ear. Unless otherwise stated, ambient sound may be divided approximately equally between parallel filter elements. The term "earbud" means an apparatus configured to fit, at least partially, within and be supported by a user's ear. Typically, a portion of an earbud fits against or within the user's outer ear canal. Other portions of an earbud may fit within the concha or pinna of the user's ear.

Such passive acoustical filters can be designed compactly in order to fit within an earbud, headphone, or other apparatus that can be placed into or outside an ear. Further, such passive acoustical filters can be designed to attenuate certain damaging and/or disturbing sound frequencies associated with specific environments and/or activities. For example, a passive acoustical filter may include a series of low-pass filter elements in parallel with a high-pass filter element and can attenuate damaging mid-range frequencies associated with attending a concert. For further example, a passive acoustical filter may provide a low-pass filter element and a high-pass filter element in parallel, and can attenuate mid-range frequencies associated with attending a sports event or participating in motor sport activities. Yet another exemplary passive acoustical filter may include a series of low-pass filter elements, and can attenuate mid and high-range frequencies associated with sounds disturbing to sleep. Other passive acoustical filters are possible that provide different types of filter elements alone, in parallel, in series, and/or in parallel/series combinations to attenuate unwanted frequencies associated with specific activities and/or environments, while allowing desired frequencies to pass through.

Figure 2:
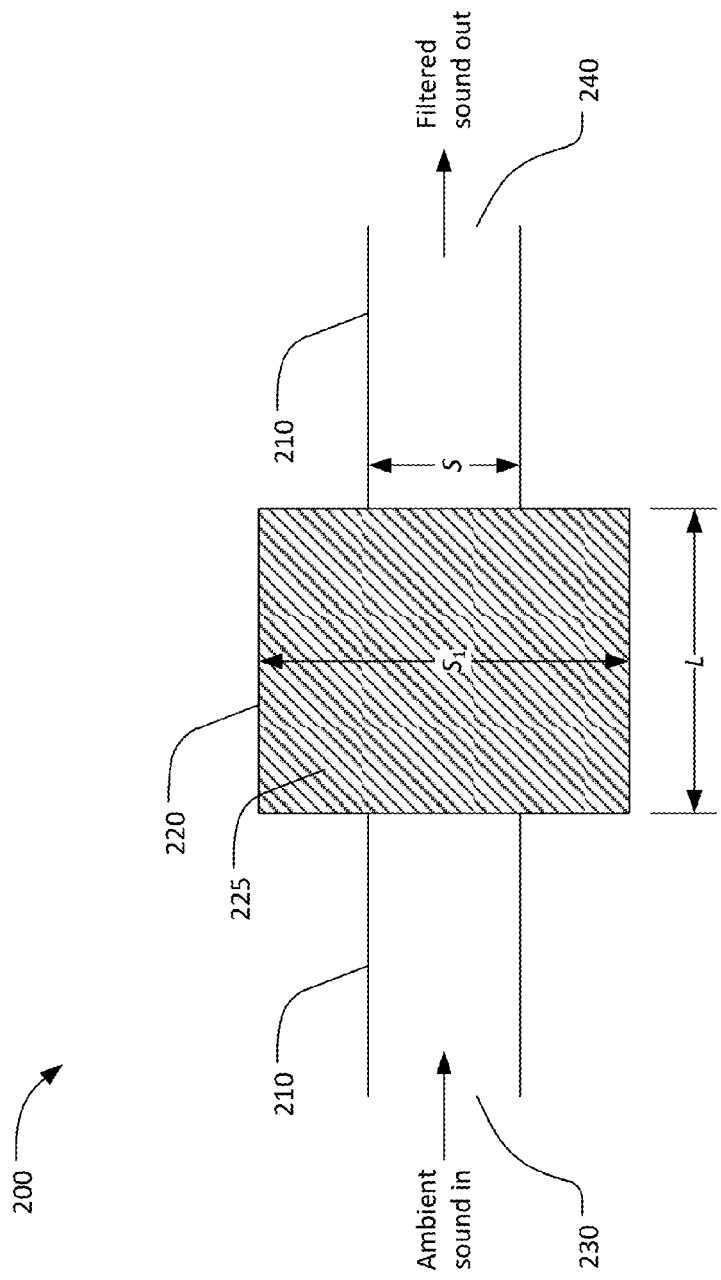
FIG. 2 is a schematic cross-sectional view of an exemplary low-pass filter element.

FIG. 2 is a schematic cross-sectional view of an exemplary low-pass filter element. The low-pass filter element 200 includes a main branch 210 and a single expansion chamber 220. The expansion chamber 220 may be filled with a insert 225. In operation, ambient sound can enter an opening 230 of the low-pass filter 200, and certain sound frequencies can be filtered as the ambient sound passes through the main branch 210 and expansion chamber 220. The resulting filtered sound can exit the opening 240 at the opposite end of the low-pass filter element 200.

The following equation can be used to calculate the dimensions needed for a low-pass filter element to achieve a desired cutoff frequency (i.e., the frequency at which the filter starts to have effect):

$$f_c = \left( \frac{cS}{\pi L (S_i - S)} \right)$$

Where:
fc=the cutoff frequency of the low-pass filter element 200;
c=speed of sound within the expansion chamber 220;
S=diameter of the main branch 210;
$S_1$=diameter of the expansion chamber 220; and
L=length of the expansion chamber 220.

The cutoff frequency of the low pass filter element 200 is dictated by the shape and size of the filter element, as well as the medium within expansion chamber of the filter element. The conduction of sound waves through a medium is dependent upon the ratio of the bulk modulus of the medium to the density of the medium, and is governed by the Newton-Laplace equation:

$$c = \sqrt{\frac{K}{\rho}}$$

Where:
c is the speed of sound;
K is the bulk modulus of the medium; and
ρ is the density of the medium.

The speed of sound in air is 343 meters per second (at 20° C., 1 atm). In some applications, the size of a filter element having a desired cutoff frequency can be reduced by filling the expansion chamber with an insert made of a material having a ratio of bulk modulus to density (K/ρ) less than that of air. Filing the expansion chamber with such a material will slow down the speed of sound. For example, in the case of a low-pass filter element, filling the expansion chamber with a material that lowers the speed of sound by a factor of two can reduce the length of the expansion chamber equally by a factor of two. A reticulated material that has a K/ρ ratio lower than air may be placed inside the acoustical filters to reduce the speed of sound, while still allowing passage of sound through the filter. In this context, "reticulated" means forming or formed like a network or a web. Suitable reticulated materials may include open-cell or closed-cell foams made of polyurethane, polyester, polystyrene, or other plastic. Other suitable reticulated materials include organic fibers like cotton, bamboo, and yarn.

Figure 3:
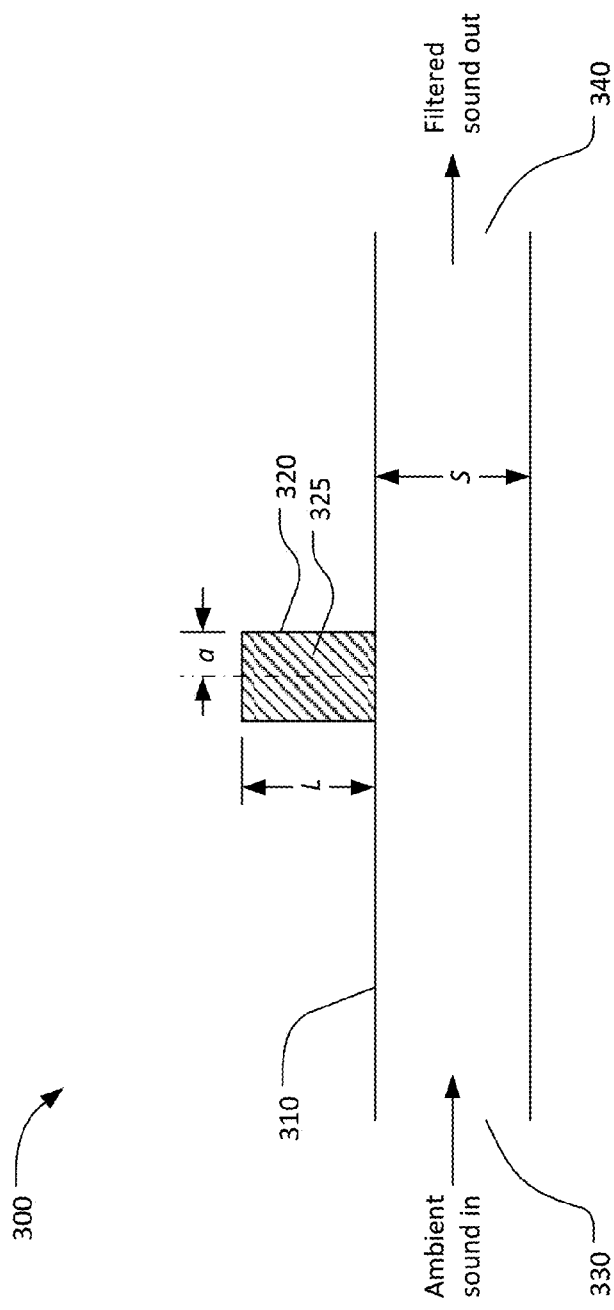
FIG. 3 is a schematic cross-sectional view of an exemplary high-pass filter element.

FIG. 3 is a schematic cross-sectional view of an exemplary high-pass filter element. The high-pass filter element 300 includes a main branch 310 and a side branch 320. The side branch may optionally be filled with an insert 325. In operation, ambient sound can enter an opening 330 of the high-pass filter element 300, and certain sound frequencies can be filtered as the ambient sound passes through the main branch 310 and side branch 320. The resulting filtered sound can exit the opening 340 at the opposite end of the high-pass filter element 300.

The following equation can be used to calculate the dimensions needed for a high-pass filter element to achieve a desired cutoff frequency:

$$f_c = \left( \frac{ca^2}{2SL} \right)$$

Where:
fc=the cutoff frequency of the high pass filter element 300;
c=speed of sound in the insert 325;
S=diameter of the main branch 310;
L=the length of the side branch 320; and
a=radius of the side branch 320.

Figure 4:
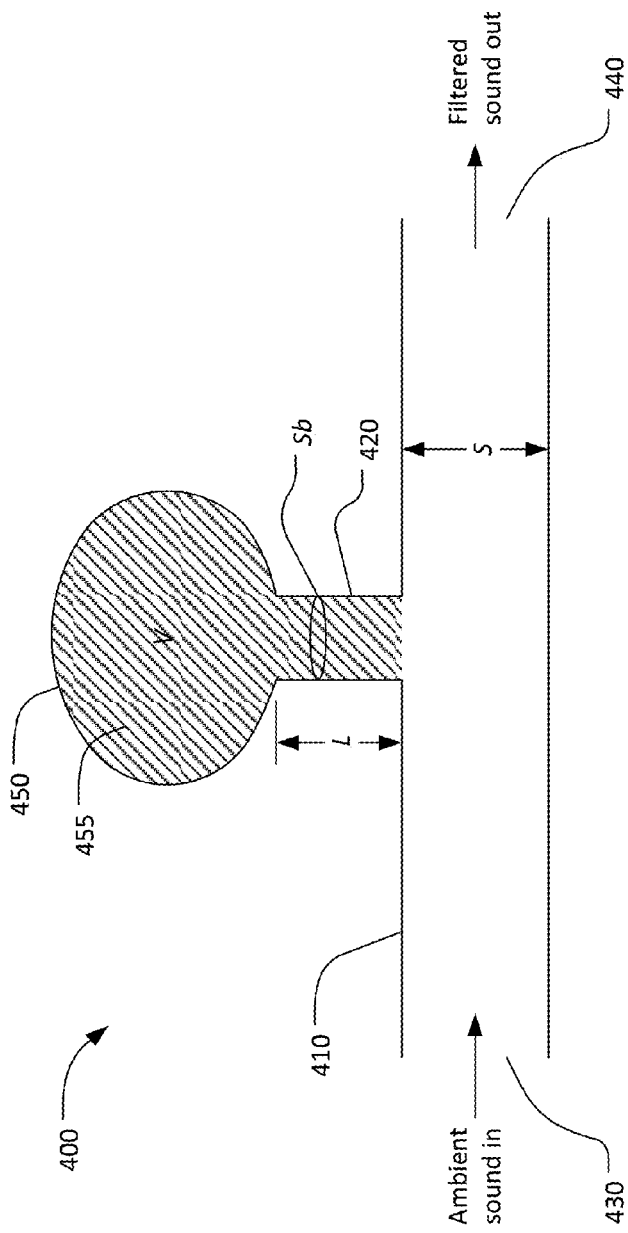
FIG. 4 is a schematic cross-sectional view of an exemplary band-reject filter element.

FIG. 4 is a schematic cross-sectional view of an exemplary band-reject filter element. The band-reject filter element 400 includes a main branch 410, a volume neck 420, and an expansion chamber 450. The expansion chamber and the volume next may be filled with an insert 455. In operation, ambient sound can enter an opening 430 of the band-reject filter element 400, and certain sound frequencies can be filtered as the ambient sound passes through the main branch 410, volume neck 420 and expansion chamber 450. The resulting filtered sound can exit the opening 440 at the opposite end of the band-reject filter element 400.

The following equation can be used to calculate the dimensions needed for a band-reject filter element to achieve a desired cutoff frequency:

$$f_c = \left(\frac{c}{2\pi}\right)\sqrt{\left(\frac{S_b}{LV}\right)}$$

Where:
fc=the cutoff frequency of the band-reject filter element 400;
c=speed of sound in the insert 455;
L=the length of the volume neck 420;
$S_b$=area of the volume neck 420; and
V=volume of the expansion chamber 450.

As will be described below, a combination of acoustical filter elements can be used to achieve a target response curve for a particular environment and/or activities that protects the ear from certain damaging or disturbing sound frequencies while allowing other sound frequencies to reach the ear.

Figure 5:
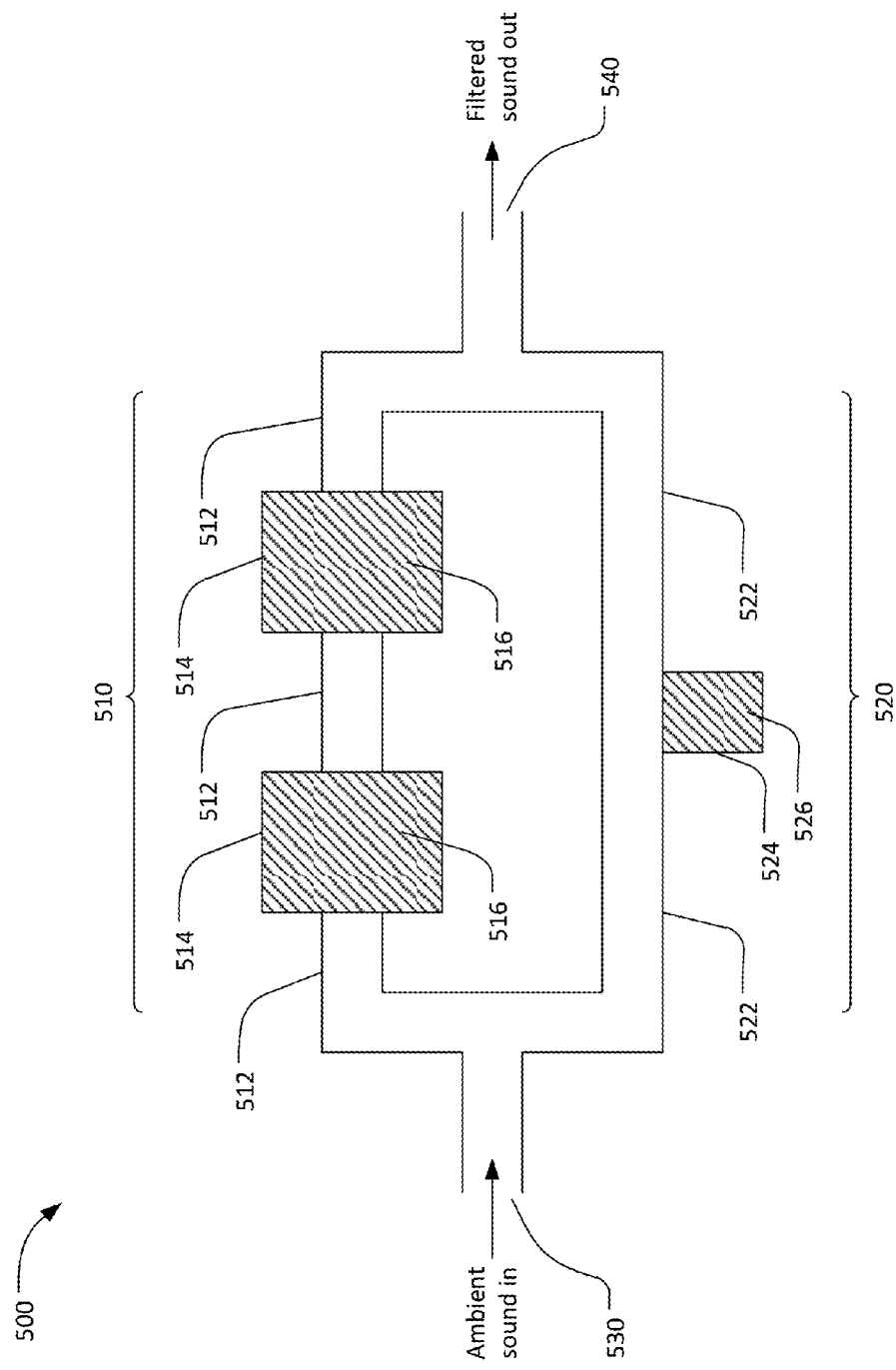
FIG. 5 is a schematic diagram of a passive acoustical filter including a series of low-pass filter elements in parallel with a high-pass filter element.

FIG. 5 is a schematic diagram of a passive acoustical filter 500 that can be used within an earbud, headphone or other apparatus to protect a human's auditory system from hearing damage and/or audio disturbance associated with attending musical events. The passive acoustical filter 500 includes a double-stage low-pass filter element 510 arranged in parallel with a single stage high-pass filter element 520. The configuration of a double-stage low-pass filter element in parallel with a single stage high-pass filter element will be referred to herein as a "music acoustical filter". The double-stage low-pass filter element 510 consists of two low-pass filter elements in series. The low-pass filter elements include respective expansion chambers 514 connected by a main branch 512. Either or both of the expansion chambers may be filled with respective inserts 516. The high-pass filter element 520 includes a main branch 522 and a side branch 524 which may be filled with an insert 526 526. In operation, ambient sound can enter the passive acoustical filter 500 at one opening 530 and certain sound frequencies can be filtered as the ambient sound passes through the high-pass filter element 520 and the dual-stage low-pass filter element 510. The resulting filtered sound can exit the passive acoustic filter 500 at the opposite opening 540. The filtered sound exiting at 540 may be approximately the sum of the sound passing through the double-stage low-pass filter element 510 and the sound passing through the high-pass filter element 520.

Exemplary dimensions for the double stage low-pass filter element 510, are set forth in Table 1 below:

TABLE 1

Exemplary dimensions for the
double-stage low-pass filter element 505

| | |
|---|---|
| Main branch 512 diameter | 0.5 mm |
| Expansion chamber 514 diameter | 2.6 mm |
| Expansion chamber 514 length | 14 mm |

These dimensions can be derived from the equation for the low-pass filter element set forth above. Further, these dimensions can be useful for creating a compact passive acoustic filter that can be inserted into ear buds, headphones or other apparatuses that fit into or outside an ear and for achieving an exemplary cutoff frequency for each low-pass filter of approximately 300 Hz. Unless otherwise stated, the term "approximately" means plus-or-minus 20%. In this example, the resonant frequencies of the two low-pass filter elements are the same. However, in other music filter designs, the resonant frequencies and dimensions of the two low-pass filter elements may differ.

Further, inserts 516 made from a reticulated material, for example a foam material having a density of 0.5 g/cm³ and bulk modulus 27 kPA, can be used the expansion chambers 514 of the low-pass filter element 510 to reduce the speed of sound (e.g., to 200 m/s). The foam material or other reticulated material can optionally be inserted in both expansion chambers 514 of the double stage low-pass filter 510 to reduce the speed of sound and to help keep the dimensions of the music acoustic filter compact. For the double-stage low-pass filter 510 having the dimensions disclosed in Table 1, filling the expansion chambers 512 with foam inserts 516 of these parameters would lower the cutoff frequency from approximately 300 Hz to approximately 200 Hz. To achieve a low-pass filter element having a cutoff frequency of 200 Hz or less without the use of a material to reduce the speed of sound in the expansion chambers, would require the length of diameter of the expansion chamber by 50% from the dimensions disclosed in Table 1. Such a double-stage low pass filter may be too large to include within an earbud.

Passive acoustical filter 500 also includes a high-pass filter element 520 having a main branch 522, and single side branch 524. Exemplary dimensions for the high-pass filter element 520, are set forth in Table 2 below:

TABLE 2

Exemplary Dimensions for
the high-pass filter element 520

| | |
|---|---|
| Side branch 524 diameter | 0.5 mm |
| Side branch 524 length | 3.0 |
| Main branch 522 diameter | 0.55 mm |

These dimensions can be derived from the equation for the high-pass filter element set forth above. Further, these dimensions can be useful for creating a compact passive acoustic filter that can be inserted into ear buds, headphones or other apparatuses that fit into or outside an ear and for achieving an exemplary cutoff frequency of approximately 18,200 Hz.

The dimensions described above for the passive acoustical filter 500 are non-limiting examples, and other dimensions that can achieve similar hearing protection may also be used. Additionally, the dimensions described above can be tailored to attenuate frequencies associated with specific genres of music. Further, the frequency response of a music acoustical filter can be selected to suit the venue of a musical event. For example, the cut-off frequencies of the low-pass filter elements may be 50 to 3000 Hz, and the cutoff frequency of the high pass filter element may be 1,000 to 25,000 Hz.

Figure 1:
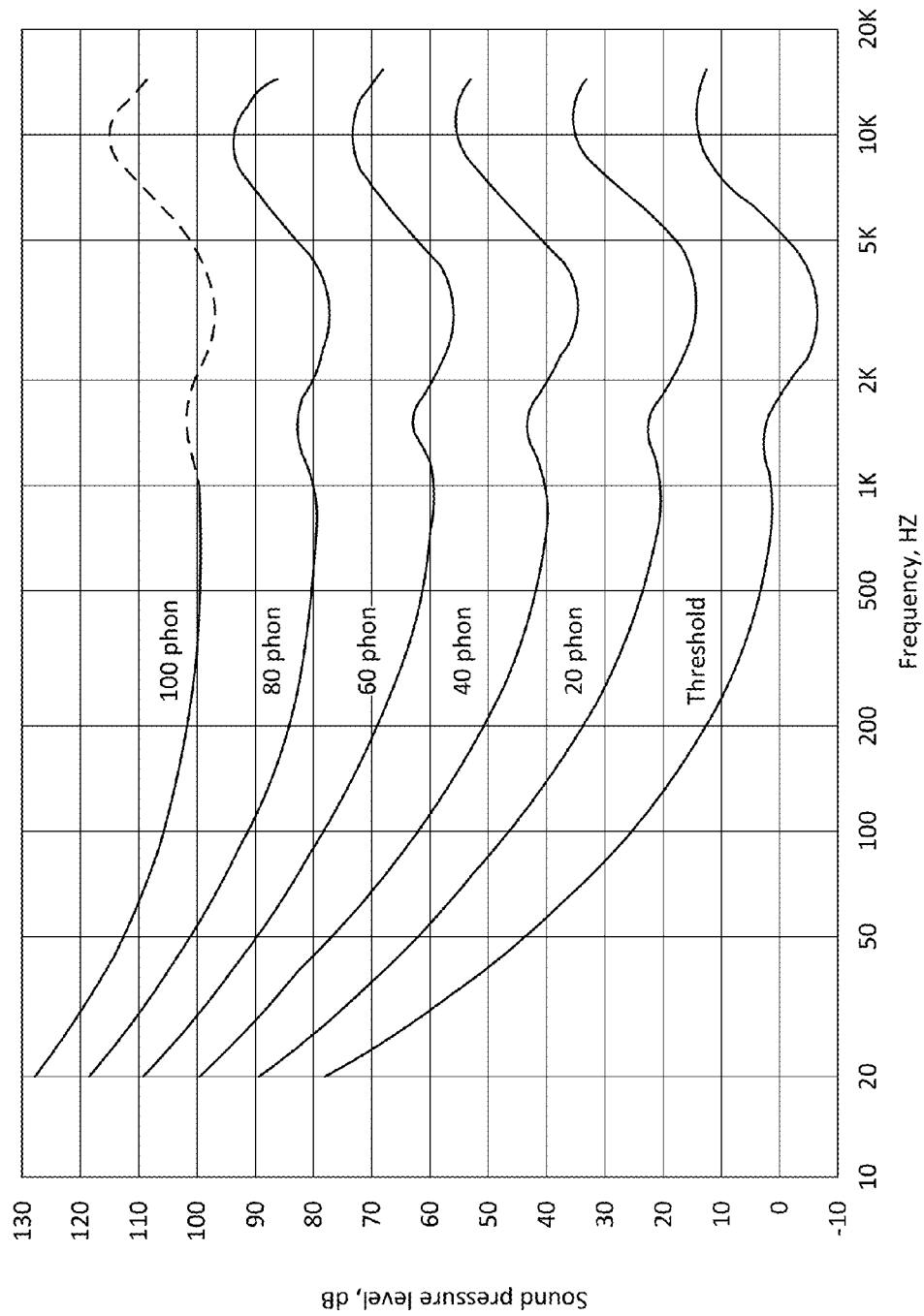
FIG. 1 is a graph of equal-loudness contours.
Figure 6:
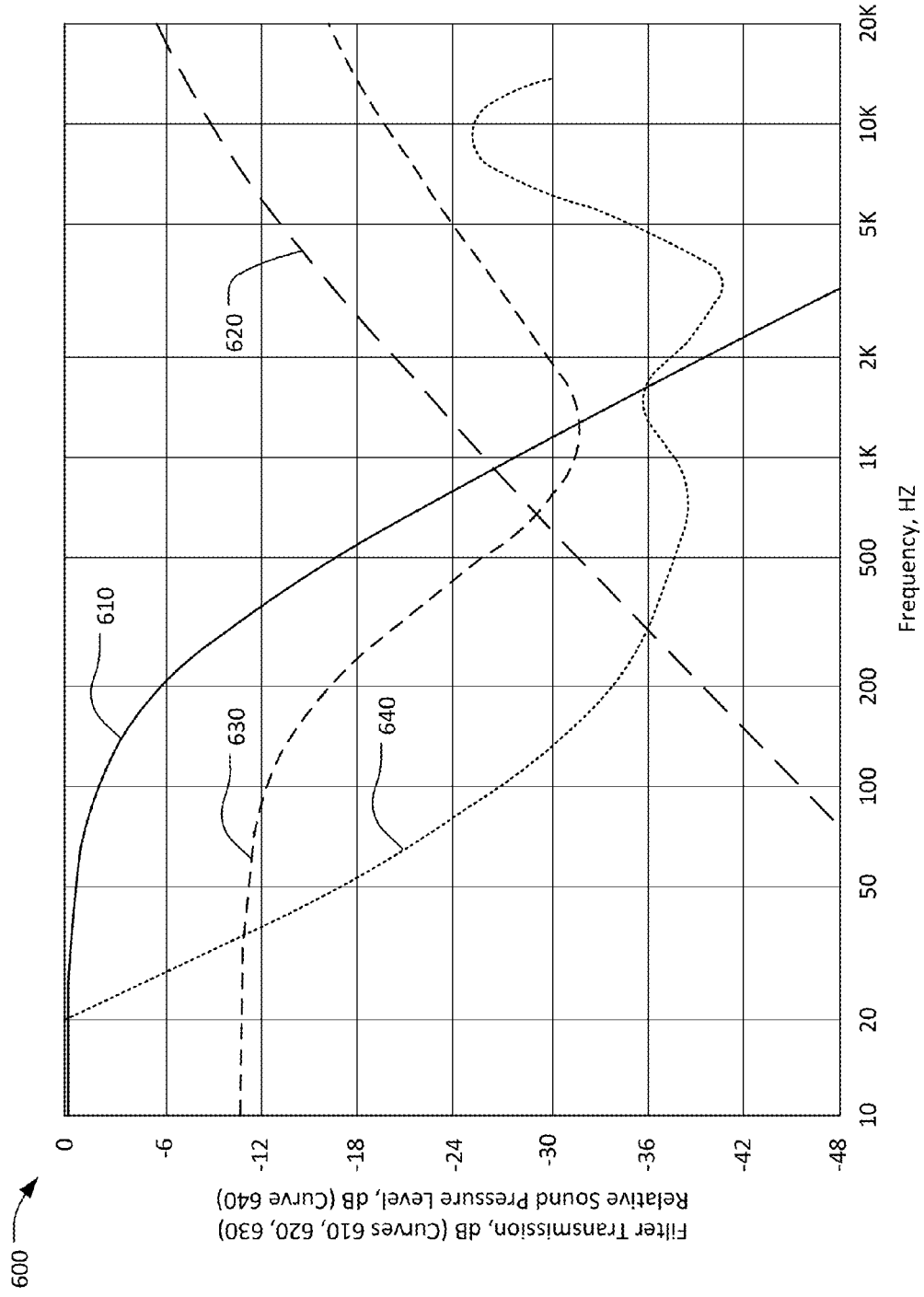
FIG. 6 is a graph of attenuation curves relating to the passive acoustical filter of FIG. 5.

FIG. 6 is a graph of transmission curves relating to a music acoustic filter having the general configuration of the passive acoustic filter 500 as shown in FIG. 5. The transmission curves are plotted along an X axis that represents sound frequency measured in hertz (Hz) and a Y axis that represents transmission (inverse of attenuation) of a passive acoustic filter or filter element measured in decibels (dB). The curve 610 represents the transmission of a loss-less double-stage low-pass filter element having the dimensions given in Table 1, including the incorporation of inserts 516 made from a reticulated material in the expansion chambers 514 of the double-stage low-pass filter elements. The curve 620 represents the transmission of a loss-less high-pass filter element having the dimensions given in Table 2. The curve 630 represents the combined transmission of the double stage low-pass filter in parallel with the single stage high-pass filter, including frequency independent attenuation that occurs in the small diameter main branches of the filter elements. The curve 640 is the 80 Phon loudness level from FIG. 1, normalized to 0 dB at 20 Hz. The curve 640 represents the sound pressure level required to produce apparently equal loudness as a function of frequency. As illustrated in FIG. 6, the performance of the passive acoustic filter (as summarized by the transmission curve 630) compliments the 80 Phon equal loudness curve 640, in that the filter provides highest attenuation (lowest transmission) at frequencies where the human ear is most sensitive, and lowest attenuation (highest transmission) for low and high frequencies where the ear is less sensitive.

Figure 7:
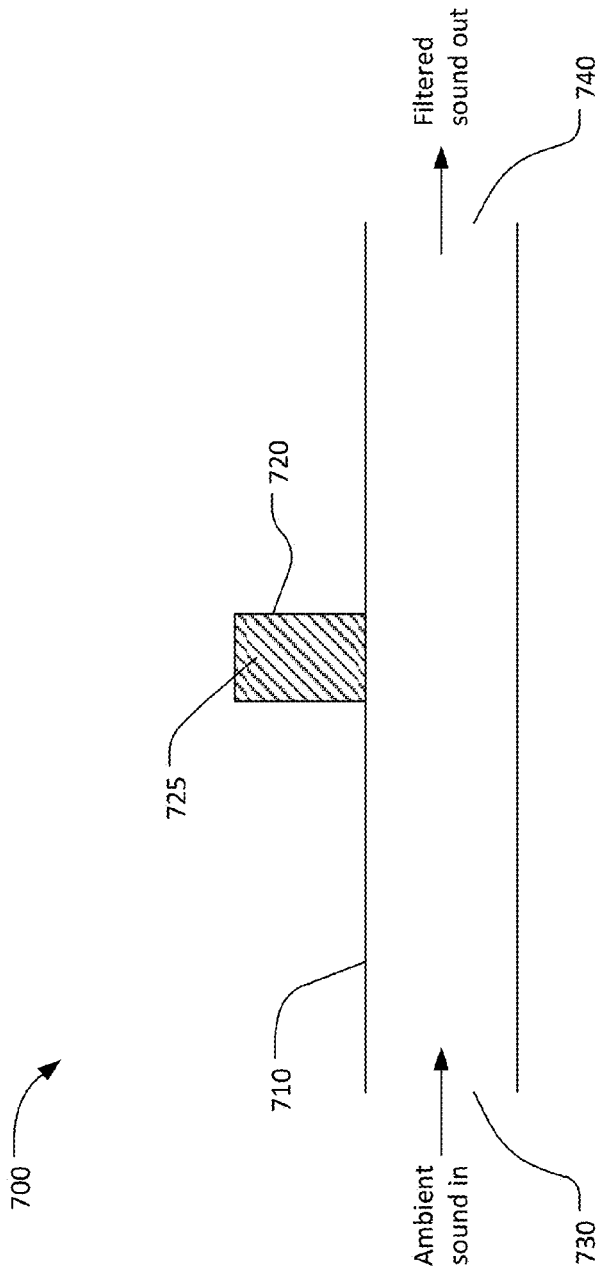
FIG. 7 is a schematic diagram of an exemplary high-pass filter element.

FIG. 7 is a schematic diagram of a passive acoustical filter 700 that can be used within an ear bud, headphone or other apparatus to protect a human's auditory system from hearing damage and/or audio disturbance associated with air and train travel. The passive acoustical filter 700 includes a single stage high-pass filter element having a main branch 710 and a side branch 720. The configuration of a single high-pass filter element will be referred to herein as a "travel acoustic filter". In operation, ambient sound can enter the passive acoustical filter 700 at one opening 730, and certain sound frequencies can be filtered as the ambient sound passes through the main branch 710 and side branch 720. The resulting filtered sound can exit the passive acoustical filter 700 at the opposite opening 740.

Exemplary dimensions for the passive acoustical filter 700, in accordance with an embodiment of the disclosed subject matter, are set forth in Table 3 below:

TABLE 3

Exemplary dimensions for the passive acoustical filter 700

| | |
|---|---|
| Side branch 720 diameter | 2 mm |
| Side branch 710 length | 20 mm |
| Main branch 710 diameter | 2 mm |

The above disclosed dimensions can be derived from the equation for the high-pass filter element set forth above. Further, these dimensions can be useful for creating a compact filter that can be inserted into earbuds, headphones or other apparatuses that fit into or outside an ear, and for achieving an exemplary cutoff frequency of approximately 1850 Hz.

An insert 725, made from a reticulated material, having dimensions approximate to the side branch 720 may optionally be placed into the side branch 720 to slow down the speed of sound and reduce the cutoff frequency to approximately 925 Hz.

The dimensions described above for the travel acoustical filter are non-limiting examples, and other dimensions that can achieve similar hearing protection may also be used.

Figure 8:
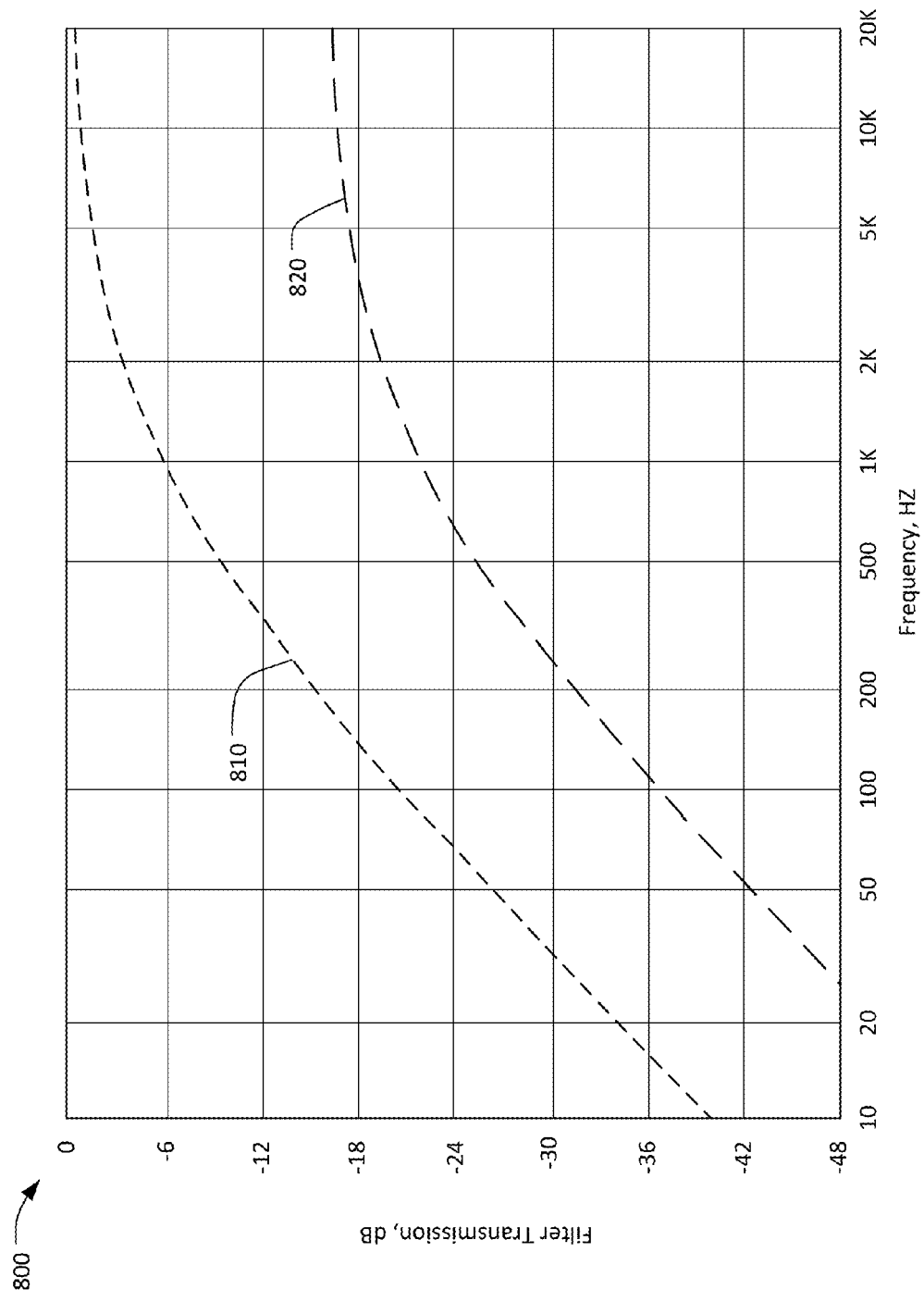
FIG. 8 is a graph of attenuation curves for two low-pass filter elements such as the low-pass filter element shown in FIG. 7.

FIG. 8 is a graph of transmission curves relating to a travel acoustic filter having the general configuration of the passive acoustic filter 700 as shown in FIG. 7. The transmission curves are plotted along an X axis that represents sound frequency measured in hertz (Hz) and a Y axis that represents transmission (inverse of attenuation) of a passive acoustic filter or filter element measured in decibels (dB). Specifically, FIG. 8, includes a curve 810 that represents the transmission of a loss-less high-pass filter (e.g., the high-pass filter shown in FIG. 7 and defined in Table 3) as a function of frequency. FIG. 8 also includes a curve 820 that represents the transmission of a realistic travel acoustic filter including attenuation that occurs in the narrow diameter main branch of the filter A travel acoustical filter can be designed to attenuate low and mid-range frequencies, while allowing high-range frequencies to pass through the filter unchanged or attenuated by a predetermined amount.

Figure 9:
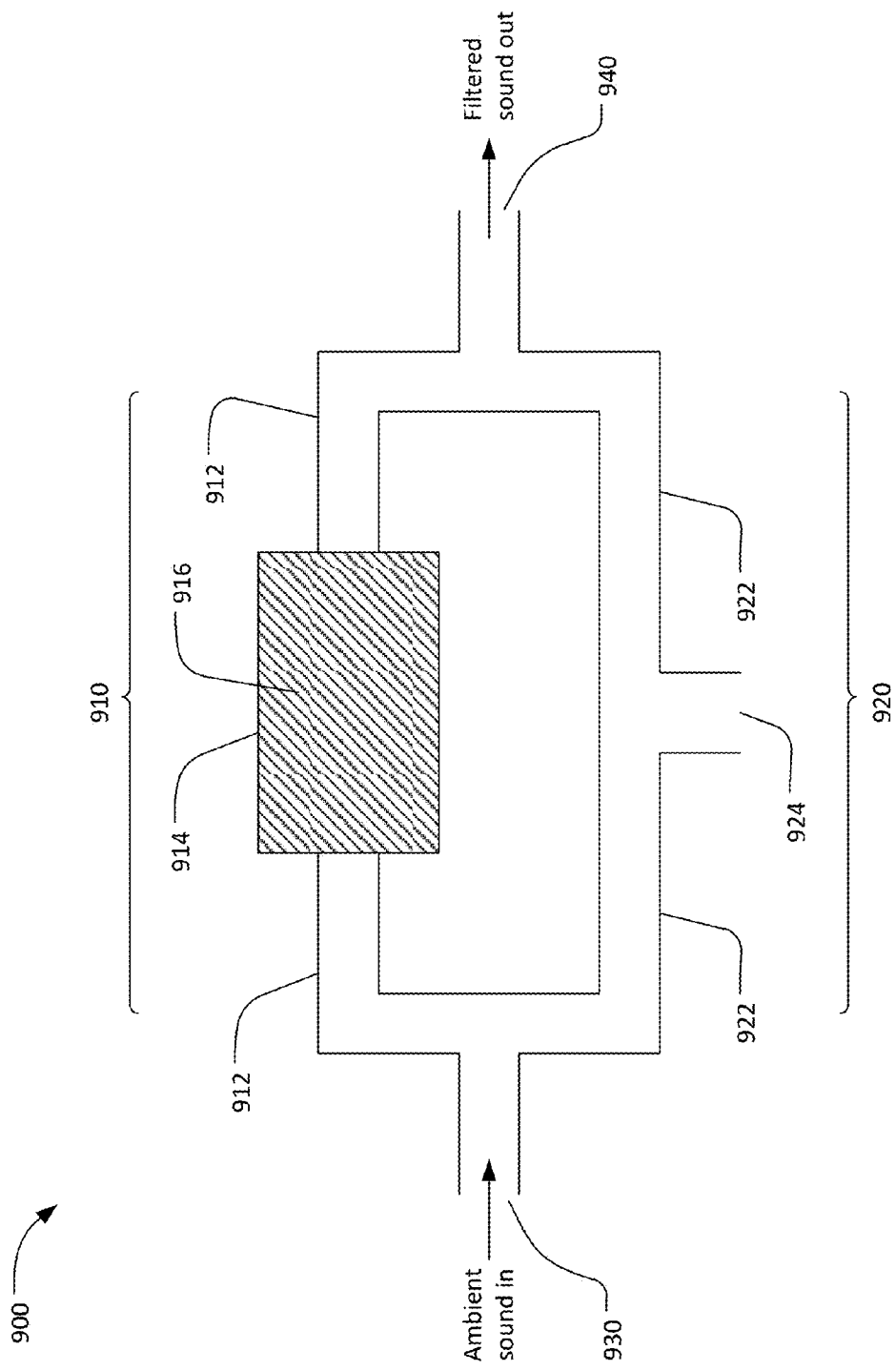
FIG. 9 is a schematic diagram of a passive acoustical filter including a low-pass filter element in parallel with a high-pass filter element.

FIG. 9 is a schematic diagram of a passive acoustical filter 900 that can be used to protect from hearing damage and/or audio disturbance associated with attending a sports event or participating in motor sport activities (e.g., jet skiing, wave running, motorcycling). The passive acoustical filter 900 includes a single stage low-pass filter element 910 and a single stage high-pass filter element 920 in parallel. The configuration of a single stage low-pass filter element and a single stage high-pass filter element in parallel will be referred to herein as a "sports filter". The low-pass filter element 910 includes a main branch 912 and an expansion chamber 914. The expansion chamber may optionally be filled with a medium 916. The high-pass filter element includes a main branch 922 and a side branch 924. In operation, ambient sound can enter the passive acoustical filter 900 at one opening 930, and certain sound frequencies can be filtered as the ambient sound passes through the low-pass filter element 910 and the high-pass filter element 920. The filtered sound can exit the passive acoustical filter 900 at the opposite opening 940.

Exemplary dimensions for the low-pass filter element 910 are set forth in Table 4 below:

TABLE 4

Exemplary Dimensions for the low-pass filter element 910

| | |
|---|---|
| Main branch 912 diameter | 0.8 mm |
| Expansion chamber 914 diameter | 5 mm |
| Expansion chamber 914 length | 12 mm |

The disclosed dimensions can be derived from the equation for the low-pass filter set forth above. Further, these dimensions can be useful for creating a compact sports filter that can be inserted into ear buds, headphones or other apparatuses that fit into or outside an ear, and for achieving an exemplary cutoff frequency for the low-pass filter element of approximately 240 Hz.

Further, a insert 916 of reticulated material having dimensions approximate to the expansion chamber 914 can optionally be placed in the expansion chamber of the low-pass filter 910 to reduce the speed of sound and thus lower the cut-off frequency of the low-pass filter element 910 to approximately 160 Hz.

Exemplary dimensions for the high-pass filter element 920 are set forth in Table 5 below:

TABLE 5

Exemplary dimensions for the high-pass filter element 920

| | |
|---|---|
| Side branch 924 diameter | 0.8 mm |
| Side branch 924 length | 12 mm |
| Main branch 922 diameter | 0.8 mm |

The disclosed dimensions can be derived from the equation for the high-pass filter set forth above. Further, these dimensions can be useful for creating a compact sports filter that can be inserted into earbuds, headphones or other apparatuses that fit into or outside an ear, and for achieving an exemplary cutoff frequency for the high-pass filter element of approximately 4.5 kHz.

The dimensions described above for the low-pass filter element 910 and the high-pass filter element 920 of the passive acoustical filter 900 are non-limiting examples, and other dimensions that can achieve similar hearing protection for sports events and motor activities may also be used. Additionally, the dimensions described above can be tailored for indoor versus outdoor sports stadium use. Because indoor stadiums generate greater midrange sound frequencies than outdoor stadiums, an indoor sports acoustical filter may be designed to attenuate more midrange frequencies (e.g., the midrange sound frequencies generated by peoples' voices) relative to the bass and treble sounds (e.g., from feet stomping, sound systems and fireworks). For example, the cut-off frequency of the low-pass filter element may be 50 to 3000 Hz, and the cutoff frequency of the high pass filter element may be 1,000 to 20,000 Hz.

Figure 10:
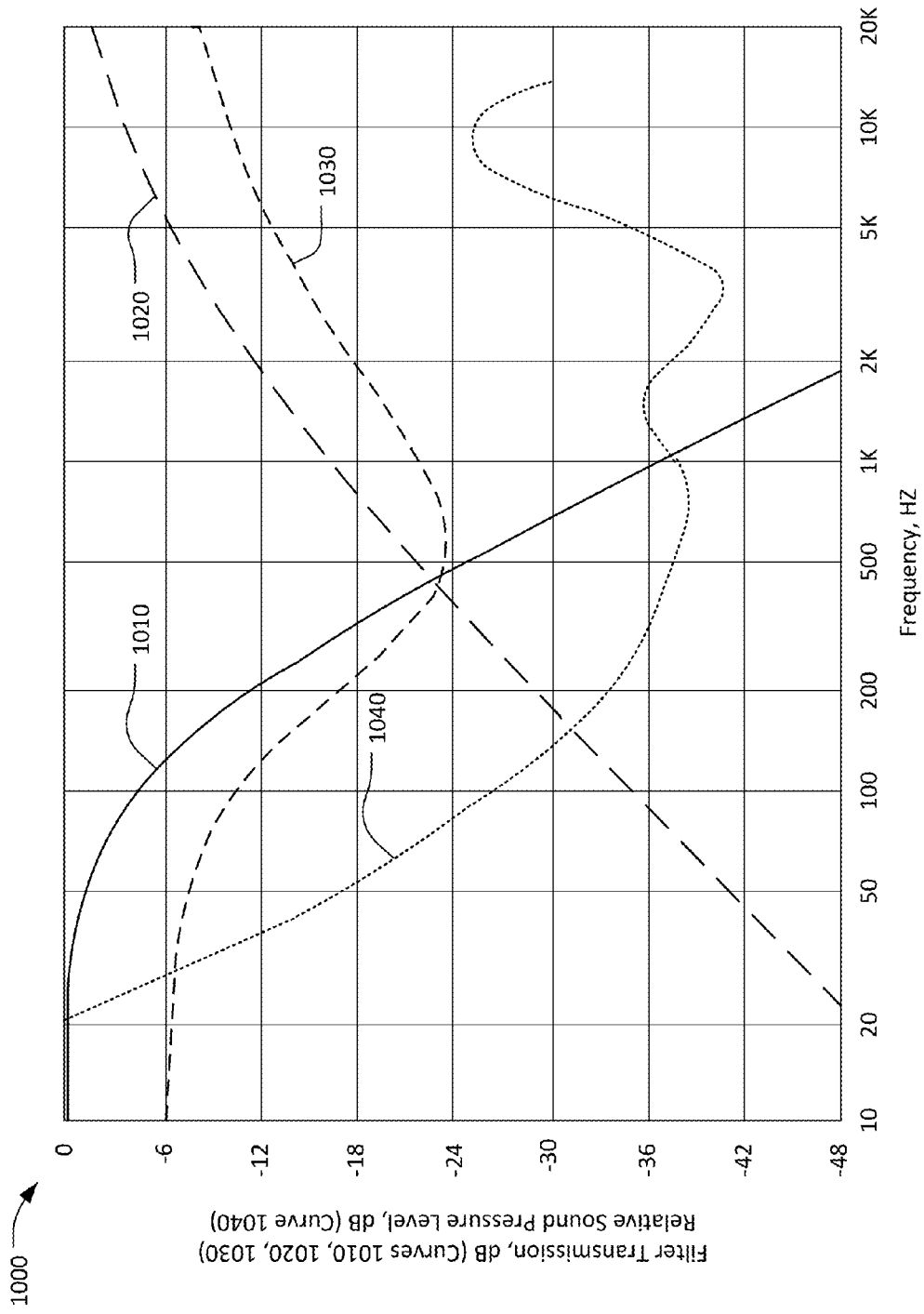
FIG. 10 is a graph of attenuation curves relating to the passive acoustical filter of FIG. 9.

FIG. 10 is a graph of transmission curves relating to a sports acoustic filter having the general configuration of the passive acoustic filter 900 as shown in FIG. 9. Like FIG. 6 and FIG. 8, the transmission curves are plotted along an X axis that represents sound frequency measured in hertz (Hz) and a Y axis that represents transmission (inverse of attenuation) of a passive acoustic filter or filter element measured in decibels (dB). The curve 1010 represents the transmission of a loss-less low-pass filter element having the dimensions given in Table 4 and the expansion chamber filled with a medium to lower the cut-off frequency to approximately 160 Hz. The curve 1020 represents the transmission of a loss-less high-pass filter element having the dimensions given in Table 5. The curve 1030 represents the combined transmission of the double stage low-pass filter in parallel with the single stage high-pass filter, including attenuation that occurs in the narrow diameter main branches of the low-pass and high-pass filter elements. The curve 1040 is the 80 Phon loudness level from FIG. 1, normalized to 0 dB at 20 Hz. The curve 1040 represents the sound pressure level required to produce apparently equal loudness as a function of frequency. As illustrated in FIG. 10, the performance of the sports acoustic filter (as summarized by the transmission curve 1030) compliments the 80 Phon equal loudness curve 1040, in that the filter provides highest attenuation (lowest transmission) at frequencies where the human ear is most sensitive, and lowest attenuation (highest transmission) for low and high frequencies where the ear is less sensitive.

Figure 11:
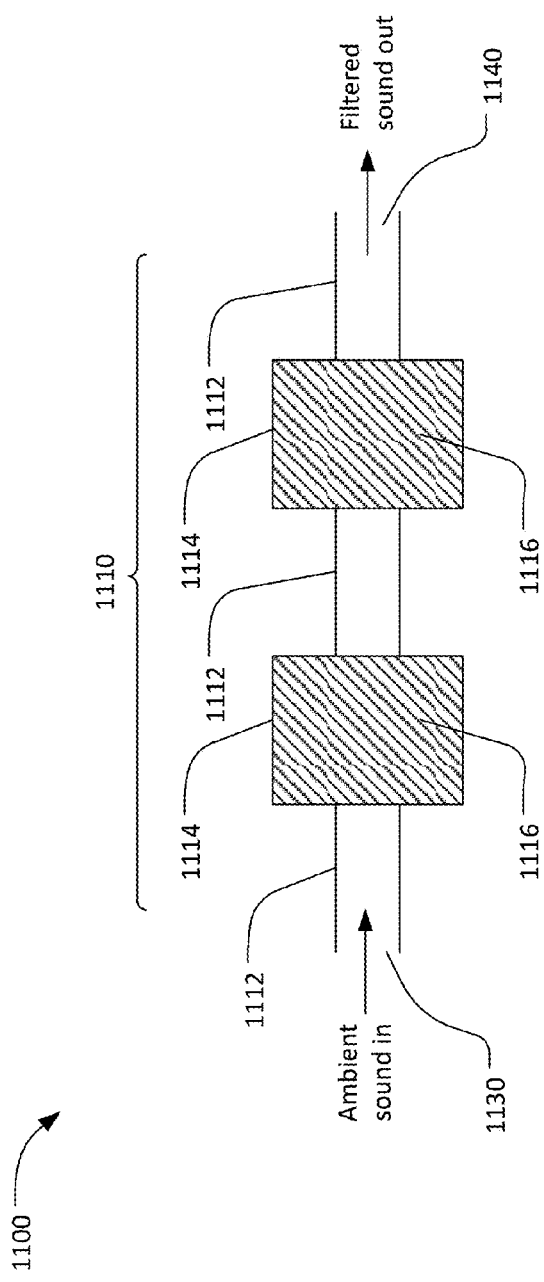
FIG. 11 is a schematic diagram of a passive acoustical filter including two low-pass filter elements in series.

FIG. 11 is a schematic diagram of a passive acoustical filter 1100 that can be used within earbuds, headphones or other apparatuses to protect a human's auditory system from auditory disturbance during sleep. Acoustical filter 1100 includes a double stage low-pass filter 1110 including two low-pass filter elements in series. A filter configuration consisting of two low-pass filter elements in series will be referred to herein as a "sleep filter". The low pass filter elements have respective expansion chambers 1114 connected by a main branch 1112. Either or both of the expansion chambers 1114 may be filled inserts 1116 made from a reticulated material. In operation, ambient sound can enter the passive acoustical filter 1100 at one opening 1130, and certain sound frequencies can be filtered as the ambient sound passes through the main branch 11112 and two expansion chambers 1114. The filtered sound can exit the passive acoustical filter 1100 at the opposite opening 1140.

Exemplary dimensions for the sleep filter, in accordance with an embodiment of the disclosed subject matter, are set forth in the table below:

TABLE 6

Exemplary Dimensions for the passive acoustical filter 1100

| | |
|---|---|
| Main branch 1112 diameter | 0.5 mm |
| Expansion chamber 1114 diameter | 4 mm |
| Expansion chamber 1114 length | 13 mm |

These dimensions can be derived from the equation for the low-pass filter set forth above. Further, these dimensions can be useful for creating a compact filter that can be inserted into earbuds, headphones or other apparatuses that fit into or outside an ear, and for achieving an exemplary cutoff frequency for the low-pass filter of approximately 130 Hz.

Further, inserts 1116 made from a reticulated material (e.g., foam) having dimensions approximate to the expansion chambers 1114 can optionally be inserted into the expansion chambers 1114 of the double stage low-pass filter 1110 to reduce the speed of sound and lower the cutoff frequency to 90 Hz.

The dimensions described above for the double stage low-pass filter of the sleep filter are non-limiting examples, and other dimensions that can achieve similar hearing protection from sleep disturbances may also be used. For example, the cut-off frequency of each low-pass filter element may be 50 to 3000 Hz.

Figure 12:
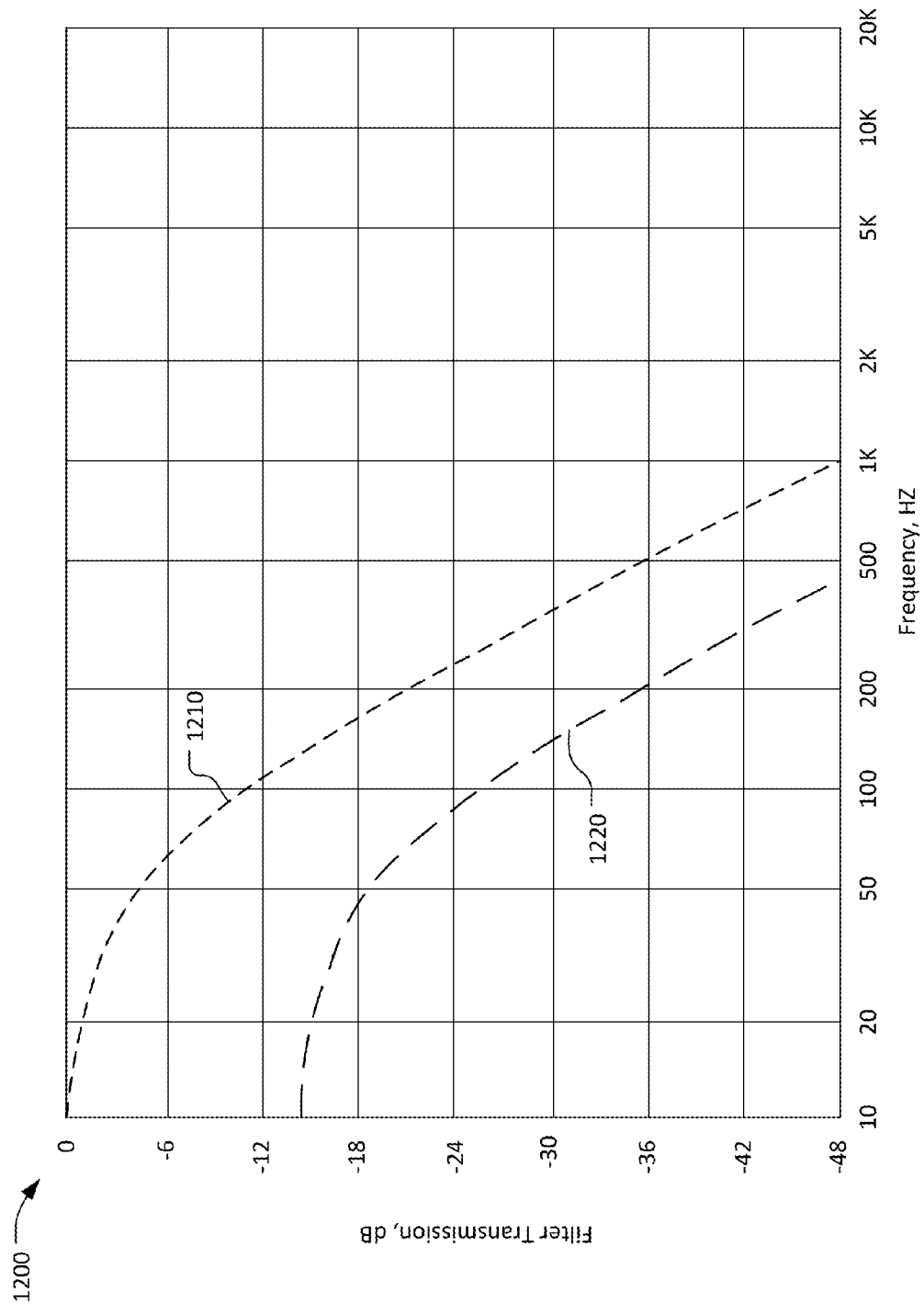
FIG. 12 is a graph of attenuation curves relating to the passive acoustical filter of FIG. 11.

FIG. 12 is a graph of transmission curves relating to a sleep acoustic filter having the general configuration of the passive acoustic filter 1100 as shown in FIG. 11. The transmission curves are plotted along an X axis that represents sound frequency measured in hertz (Hz) and a Y axis that represents transmission (inverse of attenuation) of a passive acoustic filter or filter element measured in decibels (dB). Specifically, FIG. 12 includes a curve 1210 that represents the transmission of an exemplary loss-less double-stage low-pass filter (e.g., the double stage low-pass filter shown in FIG. 11 and defined in Table 6) as a function of frequency. FIG. 12 also includes a curve 1220 that represents the transmission of the exemplary double-stage low-pass filter including attenuation that occurs in the narrow main branch of the filter and the use of the reticulated inserts to fill the expansion chambers. A sleep acoustical filter can be designed to attenuate mid- and high-range frequencies, while allowing low-range frequencies to pass through the filter unchanged or with a predetermined attenuation.

Other passive acoustical filters may include a band-reject filter element to attenuate frequencies at a specific frequency range. The dimensions of the band-reject filter element can be tailored to filter out sound at a targeted frequency range on the sound frequency spectrum. For example, a band-reject filter element, similar to the example shown in FIG. 4, can be used to filter our sound frequencies associated with a consistent whine or hum (e.g., power generation plant), while allowing other frequencies to pass through.

Other passive acoustical filters may include a band-pass filter element can be used to allow only a specific range of sound frequencies to pass through unchanged, while attenuating sounds at all other frequencies. A band-pass filter element may be realized, for example, by placing a low-pass filter element and a high-pass filter element in series, with the cutoff frequency of the high-pass filter element set lower than the cutoff frequency of the low-pass filter element.

Passive acoustical filters, such as those described above, may be disposed within a housing that can be substantially contained within the ear (e.g., in the ear canal, concha, and/or pinna. Passive acoustical filters, such as those described above, may be disposed outside the ear in a headphone apparatus or any other apparatus that allows ambient sound to travel through an acoustical filter.

Figure 13B:
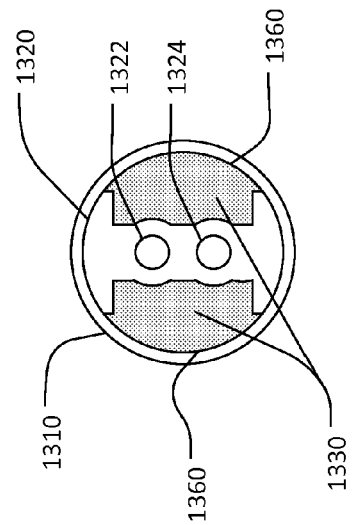
FIG. 13B is a schematic cross-sectional view of a music acoustical filter assembled form the components shown in FIG. 13A.
Figure 13A:
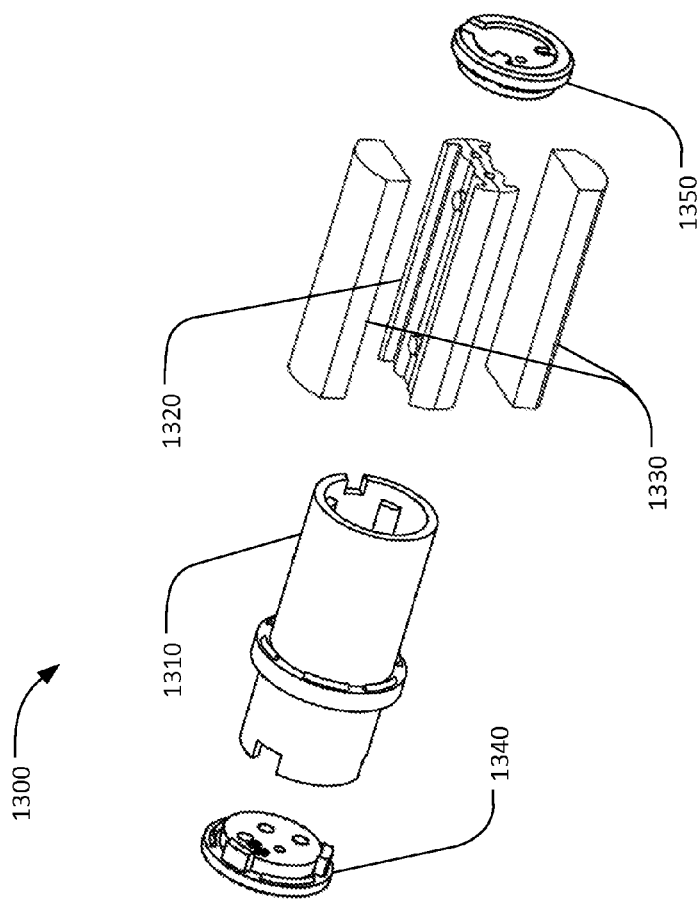
FIG. 13A is a graphical image of components of a representative music acoustical filter.

FIG. 13A is a graphical image of components of an exemplary musical acoustical filter 1300. The musical acoustic filter 1300 includes housing 1310 made of a plastic or metal material, a center divider 1320, two inserts 1330 made of foam or other reticulated material, and first and second end caps 1340, 1350. In this example, the housing 1310 is a cylindrical tube. The housing 1310 may have a cross-sectional shape other than cylindrical, such as square or hexagonal. The reticulated inserts 1330 may include an adhesive backing for attaching to the center divider 1320. The end caps 1340, 1350 incorporate apertures for the input and output of the music acoustical filter 1300 and channels that connect the other elements of the music acoustical filter 1300. In this context, the term "channels" means any passage through which acoustic waves may pass. Channels may commonly be cylindrical passages or tubes. As shown in the cross-sectional schematic view of FIG. 13B, the center divider 1320 together with the walls of the outer tube 1310 form two expansion chambers 1360 that are substantially filled by the reticulated inserts 1330. Additionally, first and second longitudinal channels 1322, 1324 run through the length the center divider 1320.

Figure 14:
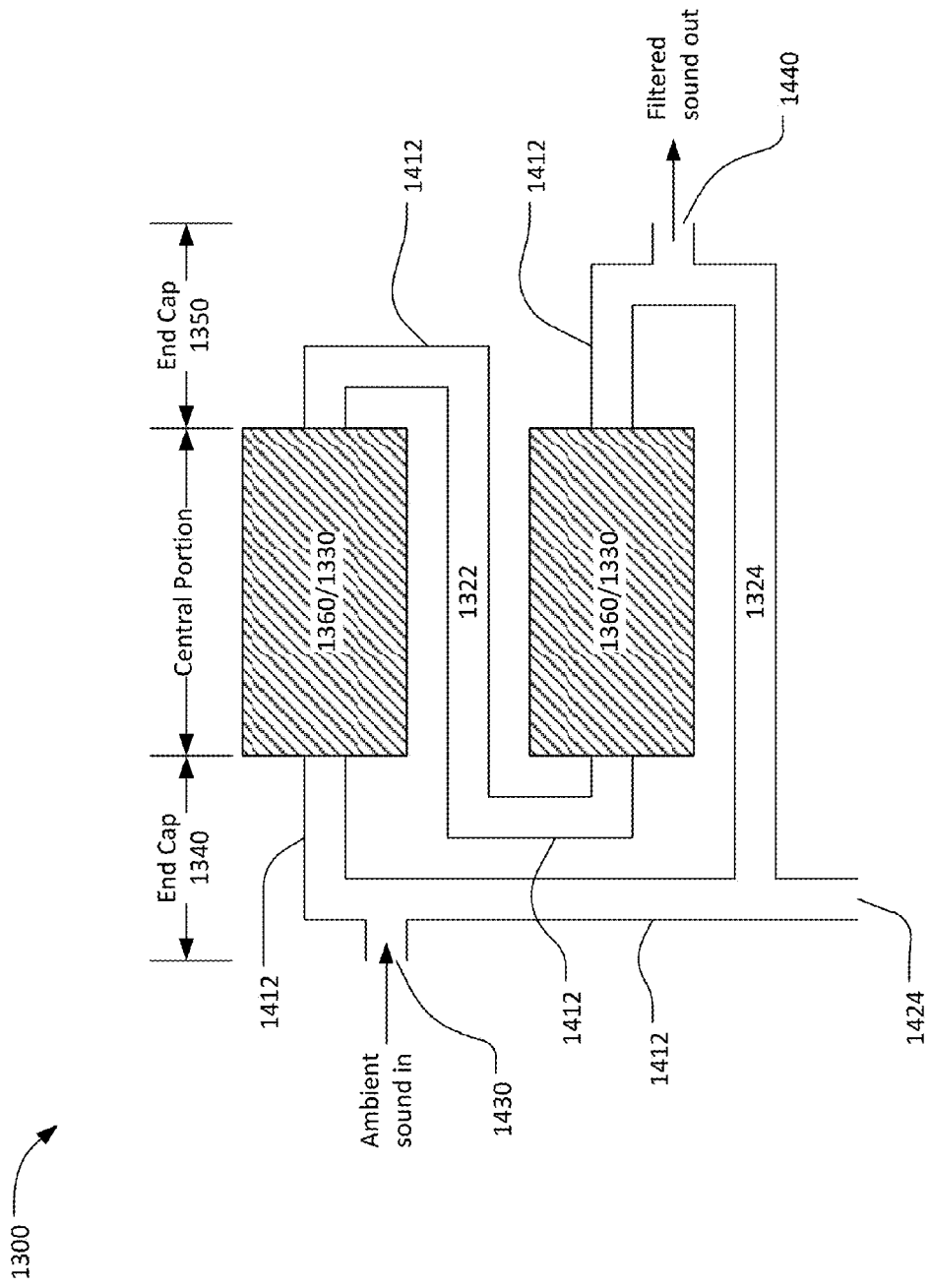
FIG. 14 is a schematic diagram of the music acoustical filter assembled form the components shown in FIG. 13A.
Figure 15:
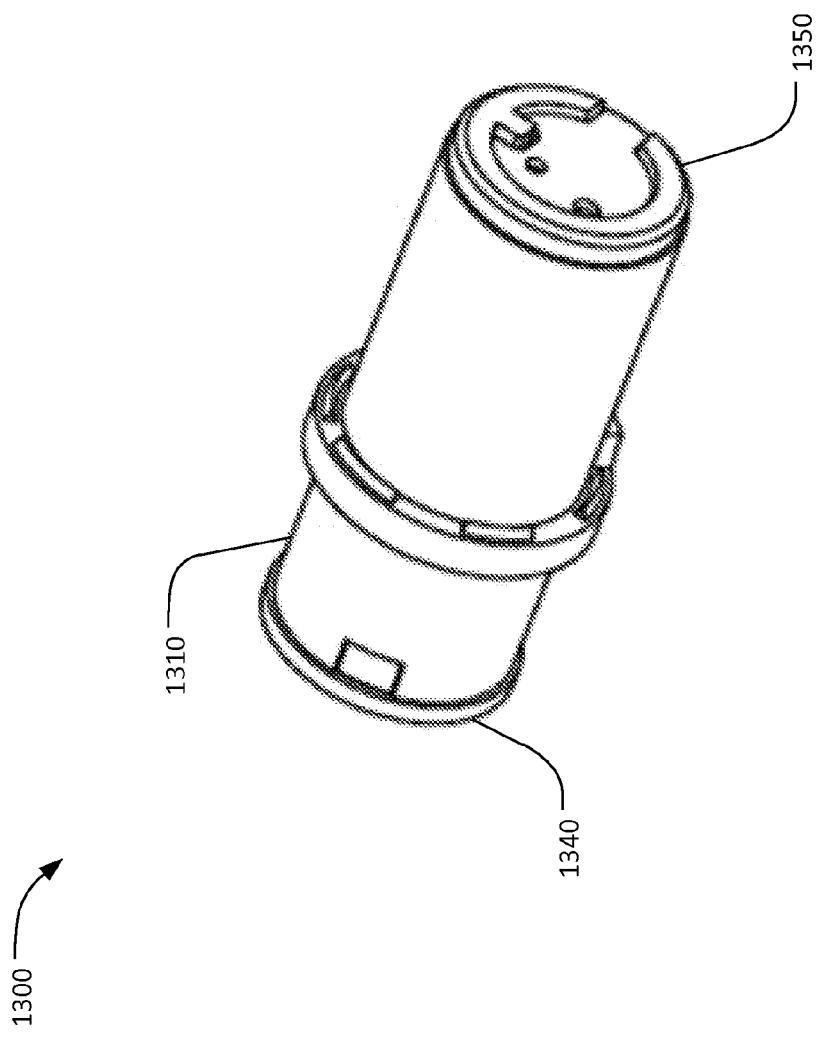
FIG. 15 is a graphical image of the passive acoustical filter assembled from the components shown in FIG. 13A.

FIG. 14 is a schematic diagram of the music acoustical filter 1300. The central portion of the device (comprising the outer tube 1310, center divider 1320, and reticulated inserts 1330, as shown in FIG. 13A) includes two expansions chambers 1360 that are substantially filled by reticulated inserts 1330. The two expansion chambers are connected in series by the first longitudinal channel 1322 (running the length of the center divider 1320) and channels 1412 (formed in the end caps 1340, 1350) to form a two-stage low pass filter. The second longitudinal channel 1324 (running the length of the center divider 1320) forms the main branch of a high-pass filter element, which is connected in parallel to the two-stage low-pass filter element by additional channels 1412 in the end caps 1340, 1350. One of the end caps (end cap 1340 as shown in FIG. 14) includes a side branch 1424 of the high-pass filter element. Ambient sound can enter the music acoustical filter 1300 through an aperture 1430 in end cap 1340 and certain sound frequencies can be filtered as the ambient sound passes through the high-pass filter element and the dual-stage low-pass filter element. The resulting filtered sound can exit the music acoustical filter 1300 through an aperture 1440 in end cap 1350. The filtered sound exiting at 1440 may be approximately the sum of the sound passing through the double-stage low-pass filter element and the sound passing through the high-pass filter element. The dimensions of the music acoustical filter 1300 may be selected to provide the desired filter function, as previously discussed with respect to the music acoustical filter 500 of FIG. 5. FIG. 15 is a graphical image of the exemplary music acoustical filter 1300 assembled from the components shown in FIG. 13A. The outer tube 1310 and end caps 1340, 1350 are visable.

Figure 16:
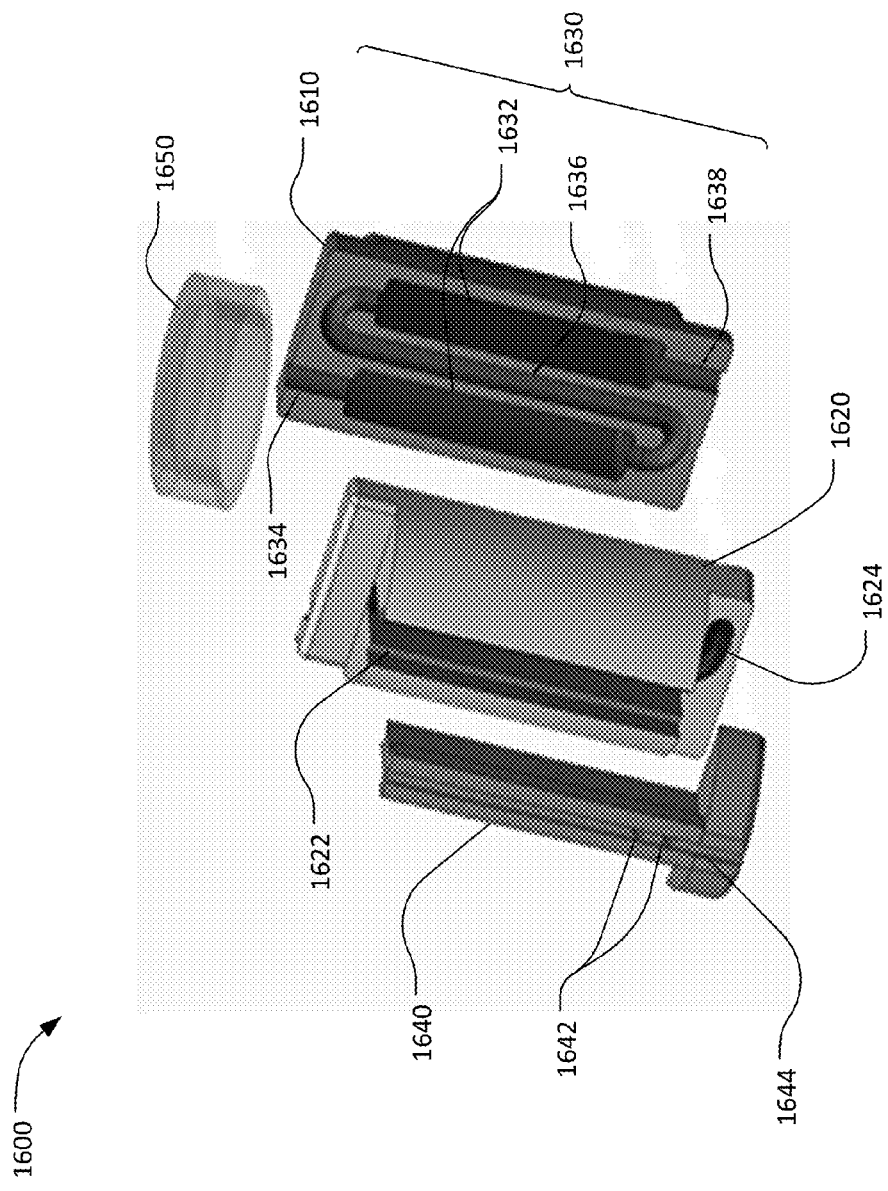
FIG. 16 is an exploded graphical image of another music acoustical filter.

FIG. 16 shows an exploded view of another exemplary music acoustical filter 1600. The exploded music acoustical filter 1600 includes a double stage low-pass filter formed by a first body piece 1610 and a second body piece 1620. The first and second body pieces 1610, 1620 may formed from a plastic material such as polycarbonate. Each of the first body piece 1610 and the second body piece 1620 includes a symmetric half of a double-stage low-pass filter element 1630 in the shape of an "S." First body piece 1610 includes half-cylindrical recesses forming two expansion chambers 1632 and connecting channels 1634, 1636, 1638. Second body piece 1620 includes mirror images recesses (not visible). When assembled, the first body piece 1610 and the second body piece 1620 collectively form two cylindrical expansion chambers connected in series by cylindrical main channels.

The second body piece 1620 also includes a cavity 1622 for placement of an insert 1640 which may be formed from polycarbonate or another plastic. When the insert 1640 is placed into the cavity 1622, an interstitial space between the insert 1640 and the second body piece 1620 forms a main branch of a high-pass filter element. A side branch of the high-pass filter element is formed by the two holes 1642. Two holes are used in this example to provide sufficient cross-sectional area for the side branch. A passage 1624 in the body piece 1620 may couple the high-pass filter element to the channel 1638. A groove 1644 in the insert 1640 provides an outlet to the ambient for the side branch of the high-pass filter element.

An end cap 1650 may fit over the end portions of first and second body pieces 1610 and 1620 to hold the pieces in alignment. The end cap may optionally include a scrim cloth designed to protect the filter from ear surface contaminants.

Figure 17:
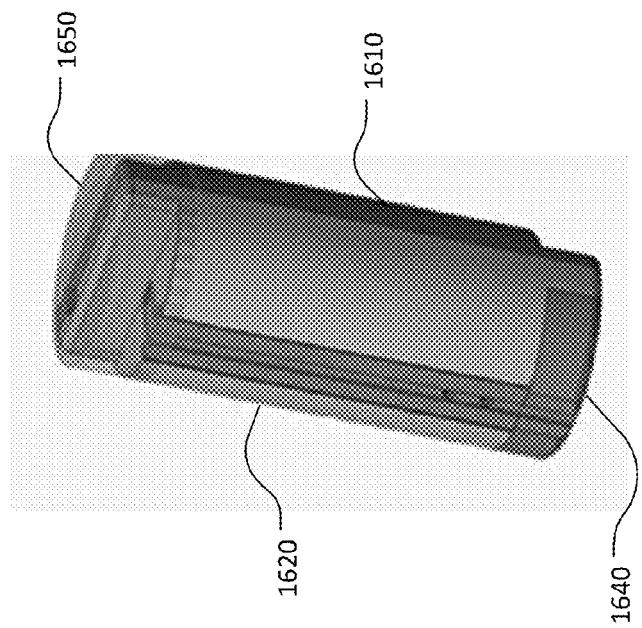
FIG. 17 is a graphical image of the music acoustical filter assembled from the components shown in FIG. 16.

FIG. 17 shows the exemplary music filter 1600 assembled from the components shown in FIG. 16. FIG. 17 shows the first body piece 1610, the second body piece 1620, the inset 1640, and the end cap 1650.

Figure 18:
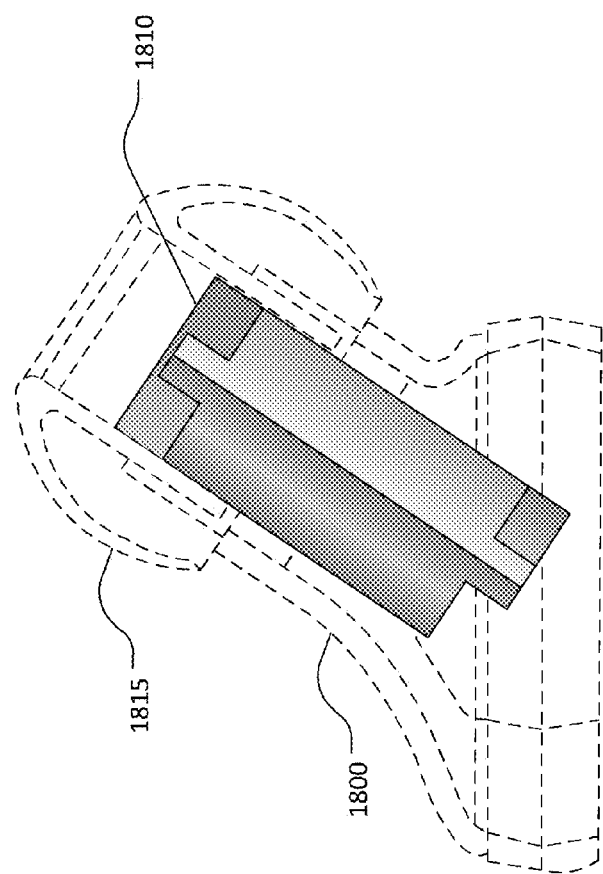
FIG. 18 is a graphical image of an exemplary music acoustical filter within an earbud.

FIG. 18 shows a transparent view of an exemplary earbud 1800 containing a passive acoustical filter 1810, which may be, for example, the music acoustic filter 1600 (as shown in FIG. 17) or the music acoustical filter 1300 (as shown in FIG. 15). The music acoustical filter 1810 is shown inserted into the neck of the exemplary earbud 1800. An outer removable cap 1815 may be positioned on top of the filter and can be inserted into the ear. The exemplary earbud 1800 may be, for example, the earbud described in Design patent application Ser. No. 29/485,359.

Passive acoustical filters as described above can be designed to be interchangeable, so they can each fit into the same sized earbud, headphone or other apparatus. Designing various passive acoustic filters for interchangeability can allow for the different types of acoustic filters to be swapped in and out of the earbud, headphone or other apparatus, in order to match the type of auditory protection desired for different environments and/or activities.

Closing Comments

Throughout this description, the embodiments and examples shown should be considered as exemplars, rather than limitations on the apparatus and procedures disclosed or claimed. Although many of the examples presented herein involve specific combinations of elements, it should be understood that those elements may be combined in other ways to accomplish the same objectives. Elements and features discussed only in connection with one embodiment are not intended to be excluded from a similar role in other embodiments.

As used herein, "plurality" means two or more. As used herein, a "set" of items may include one or more of such items. As used herein, whether in the written description or the claims, the terms "comprising", "including", "carrying", "having", "containing", "involving", and the like are to be understood to be open-ended, i.e., to mean including but not limited to. Only the transitional phrases "consisting of" and "consisting essentially of", respectively, are closed or semi-closed transitional phrases with respect to claims. Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. As used herein, "and/or" means that the listed items are alternatives, but the alternatives also include any combination of the listed items.

It is claimed:

1. A passive acoustical filter to be coupled between an ambient and an ear of a listener, comprising:

a double-stage low-pass filter comprising a first low-pass filter element in series with a second low-pass filter element, expansion chambers of the first low-pass filter element and the second low pass filter element filled with respective inserts made from a material in which a speed of sound is lower than a speed of sound in air.

2. The passive acoustical filter of claim 1, wherein the material in which the speed of sound is lower than the speed of sound in air is a reticulated material.

3. The passive acoustical filter of claim 2, wherein the reticulated material is selected from a plastic foam material, cotton fibers, bamboo fibers, and yarn.

4. The passive acoustical filter of claim 1, wherein the double-stage low-pass filter is coupled in parallel with a high-pass filter element.

5. A passive acoustical filter to be coupled between an ambient and an ear of a listener, comprising:
   a high pass filter element; and
   a low-pass filter element in parallel with the high-pass filter element, an expansion chamber of the low-pass filter element filled with an insert made from a material in which the speed of sound is lower than a speed of sound in air.

6. The passive acoustical filter of claim 5, wherein the material in which the speed of sound is lower than the speed of sound in air is a reticulated material.

7. The passive acoustical filter of claim 6, wherein the reticulated material is selected from a plastic foam material, cotton fibers, bamboo fibers, and yarn.

8. A passive acoustical filter comprising:
   an earbud including a first opening to receive sound from an ambient and a second opening to output filtered sound to an ear of a listener; and
   a low-pass filter element contained within the earbud and coupled between the first opening and the second opening, the low-pass filter element comprising an expansion chamber filled with an insert made from a material in which a speed of sound is lower than a speed of sound in air; and
   a high-pass filter element contained within the earbud and coupled in parallel with the low-pass filter element,
   wherein a cutoff frequency of the low-pass filter element is equal to or less than 200 Hz.

9. The passive acoustical filter of claim 8, wherein the material in which the speed of sound is lower than the speed of sound in air is a reticulated material.

10. The passive acoustical filter of claim 9, wherein the reticulated material is selected from a plastic foam material, cotton fibers, bamboo fibers, and yarn.

11. A passive acoustical filter, comprising:
    an earbud having a first opening to receive sound from an ambient and a second opening to output filtered sound to an ear of a user; and
    a double-stage low-pass filter contained within the earbud and coupled between the first opening and the second opening, the double-stage low-pass filter comprising a first-low-pass filter element in series with a second low-pass filter element, the first and second low-pass filter elements respectively comprising first and second expansion chambers filled with respective inserts made from a material in which the speed of sound is lower than the speed of sound in air,
    wherein cutoff frequencies of both the first low-pass filter element and the second low pass filter element are equal to or less than 200 Hz.

12. The passive acoustical filter of claim 11, wherein the double-stage low-pass filter is coupled in parallel with a high-pass filter element.

13. The passive acoustical filter of claim 11, wherein the material in which the speed of sound is lower than the speed of sound in air is a reticulated material.

14. The passive acoustical filter of claim 13, wherein the reticulated material is selected from a plastic foam material, cotton fibers, bamboo fibers, and yarn.

\* \* \* \* \*